US009701729B2

(12) United States Patent
Fukaya et al.

(10) Patent No.: US 9,701,729 B2
(45) Date of Patent: Jul. 11, 2017

(54) PEPTIDE HAVING 5 LINKED CTL EPITOPES

(71) Applicant: TAIHO PHARMACEUTICAL CO., LTD., Tokyo (JP)

(72) Inventors: Satoshi Fukaya, Ibaraki (JP); Toshihiro Osada, Ibaraki (JP); Hiroshi Wada, Ibaraki (JP); Teruhiro Utsugi, Ibaraki (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/773,140

(22) PCT Filed: Mar. 5, 2014

(86) PCT No.: PCT/JP2014/055555
§ 371 (c)(1),
(2) Date: Sep. 4, 2015

(87) PCT Pub. No.: WO2014/136814
PCT Pub. Date: Sep. 12, 2014

(65) Prior Publication Data
US 2016/0017014 A1 Jan. 21, 2016

(30) Foreign Application Priority Data
Mar. 8, 2013 (JP) ................ 2013-047271

(51) Int. Cl.
*C07K 14/00* (2006.01)
*C07K 14/47* (2006.01)
*A61K 39/00* (2006.01)
*C07K 14/82* (2006.01)

(52) U.S. Cl.
CPC ...... *C07K 14/4748* (2013.01); *A61K 39/0011* (2013.01); *C07K 14/82* (2013.01); *A61K 2039/572* (2013.01); *A61K 2039/70* (2013.01); *C07K 2319/00* (2013.01); *C07K 2319/33* (2013.01)

(58) Field of Classification Search
None
See application file for complete search history.

(56) References Cited

U.S. PATENT DOCUMENTS

| 6,719,976 | B1 | 4/2004 | Sone et al. | |
| 7,718,614 | B2* | 5/2010 | Itoh | A61K 31/565 424/185.1 |
| 9,102,715 | B2* | 8/2015 | Itoh | A61K 39/005 |
| 2002/0128201 | A1 | 9/2002 | Itoh | |
| 2003/0175288 | A1 | 9/2003 | Itoh | |
| 2004/0044188 | A1 | 3/2004 | Feige et al. | |
| 2006/0140968 | A1 | 6/2006 | Itoh et al. | |
| 2008/0014636 | A1 | 1/2008 | Sato et al. | |
| 2008/0286228 | A1 | 11/2008 | Tarantolo et al. | |
| 2010/0062010 | A1 | 3/2010 | Nishihara et al. | |
| 2010/0278851 | A1 | 11/2010 | Itoh et al. | |
| 2010/0297187 | A1 | 11/2010 | Stoloff et al. | |
| 2013/0164314 | A1 | 6/2013 | Itoh et al. | |

FOREIGN PATENT DOCUMENTS

| CN | 1218412 A | 6/1999 |
| CN | 101854945 A | 10/2010 |
| EA | 005404 B1 | 2/2005 |
| EP | 0923940 B1 | 6/1999 |
| EP | 2196209 A1 | 6/2010 |
| JP | 11-318455 A | 11/1999 |
| JP | 2002-527050 A | 8/2002 |
| JP | 2003-000270 A | 1/2003 |
| JP | 2003-512057 A | 4/2003 |
| JP | 2010-000083 A | 1/2010 |
| JP | 2012-158597 A | 8/2012 |
| RU | 2466737 C2 | 10/2011 |
| WO | WO 97/32600 A1 | 9/1997 |
| WO | WO 00/12701 A1 | 3/2000 |
| WO | WO 00/21551 A1 | 4/2000 |
| WO | WO 01/11044 A1 | 2/2001 |
| WO | WO 01/29220 A2 | 4/2001 |
| WO | WO 01/41741 A1 | 6/2001 |
| WO | WO 02/10369 A1 | 2/2002 |
| WO | WO 2004/029248 A1 | 4/2004 |
| WO | WO 2008/007711 A1 | 1/2008 |
| WO | WO 2009/038026 A1 | 3/2009 |
| WO | WO 2012/005161 A1 | 1/2012 |

OTHER PUBLICATIONS

Freshney (Culture of Animal Cells, A Manual of Basic Technique, Alan R. Liss, Inc., 1983, New York, p4).*
Dermer (Bio/Technology, 1994, 12:320).*
Gura (Science, 1997, 278:1041-1042).*
Jain (Sci. Am., 1994, 271:58-65).*
Ezzell (J. NIH Res. 1995 7:46).*
Spitler (Cancer Biotherapy, 1995, 10:1-3).*
Boon (Adv. Can. Res. 1992 58:177-210).*
Nelson et al., Ann. Intern Med. 2009; 151:727-737.*
Kataja et al., Ann Oncol 2009; 20(sup 4): iv10-14.*
Haigh et al Oncology vol. 13 p. 1561 (1999).*
Balmana et al. Ann Oncol 2009; 20(supp 4):iv19-20.*
International Search Report dated Jun. 17, 2014, in PCT/JP2014/055555.
Taiwanese Office Action dated Jan. 21, 2015 in TW 103108019.
Ishioka et al., "Utilization of MHC Class I Transgenic Mice for Development of Minigene DNA Vaccines Encoding Multiple HLA-Restricted CTL Epitopes," The Journal of Immunology, 1999, 162:3915-1925.

(Continued)

*Primary Examiner* — Sheela J Huff
(74) *Attorney, Agent, or Firm* — Foley & Lardner LLP

(57) ABSTRACT

This invention provides a cancer antigen peptide that can be administered to a wide range of cancer patients in the form of a peptide vaccine for cancer without the need for HLA typing and regardless of the HLA types of patients. Such peptide having 5 linked CTL epitopes is obtained by linking 5 CTL epitope peptides selected from among CTL epitope peptides derived from tumor antigen molecules that are reported to have the capacity for CTL induction via linkers.

6 Claims, 2 Drawing Sheets

(56) References Cited

OTHER PUBLICATIONS

Noguchi et al., "Assessment of immunological biomarkers in patients with advanced cancer treated by personalized peptide vaccination," Cancer Biology & Therapy, Dec. 15, 2010, 10(12):1266-1279.

Noguchi et al., "A randomized phase II trial of personalized peptide vaccine plus low dose estramustine phosphate (EMP) versus standard dose EMP in patients with castration resistant prostate cancer," Cancer Immunol. Immunother., 2010, 59:1001-1009.

Rosenberg et al., "Cancer immunotherapy: moving beyond current vaccines," Nature Medicine, Sep. 2004, 10(9):909-915.

Sette et al., "Nine major HLA class I supertypes account for the vast preponderance of HLA-A and -B polymorphism," Immunogenetics, 1999, 50:201-212.

Terasaki et al., "Phase I Trial of a Personalized Peptide Vaccine for Patients Positive for Human Leukocyte Antigen-A24 With Recurrent or Progressive Glioblastoma Multiforme," Journal of Clinical Oncology, Jan. 20, 2011, 29(3):337-344.

Yanagimoto et al., "Immunological evaluation of personalized peptide vaccination with gemcitabine for pancreatic cancer," Cancer Sci., Apr. 2007, 98(4):605-611.

Office Action dated Mar. 8, 2016, in JP 2015-504352.

Ishioka et al., "Utilization of MHC Class I Transgenic Mice for Development of Minigene DNA Vaccines Encoding Multiple HLA-Restricted CTL Epitopes," The Journal of Immunology, 1999, 162:3915-3925.

Search Report dated Oct. 19, 2016 in EP 14761112.3.

Office Action and Search Report dated Aug. 29, 2016, in RU 2015142659, with English translation.

International Search Report dated Jan. 20, 2015, in PCT/JP2014/077807.

Lee et al., "Increased Vaccine-Specific T Cell Frequency After Peptide-Based Vaccination Correlates with Increased Susceptibility to In Vitro Stimulation But Does Not Lead to Tumor Regression," The Journal of Immunology, 1999, 163:6292-6300.

Skosyrev et al., "The dependence of stability of the green fluorescent protein-obelin hybrids on the nature of their constituent modules and the structure of the amino acid linker," Bioorg. Khim., Sep.-Oct. 2001, 27(5):364-371, with English translation.

Zhao et al., "Balancing the Pharmacokinetics and Pharmacodynamics of Interferon-$\alpha$2b and Human Serum Albumin Fusion Protein by Proteolytic or Reductive Cleavage Increases in Vivo Therapeutics Efficacy," Mol. Pharm., 2012, 9(3):664-670.

\* cited by examiner

Fig. 1

| Peptide | Epitope specific CTL induction | | | | |
|---|---|---|---|---|---|
| | N terminus | | | | C terminus |
| TPV01 | PEP5 | PEP2 | PEP4 | PEP7* | PEP3 |
| TPV02 | PEP5 | PEP2 | PEP7* | PEP3 | PEP4 |
| TPV03 | PEP4 | PEP6 | PEP5 | PEP7* | PEP3 |
| TPV04 | PEP5 | PEP2 | PEP4 | PEP6 | PEP3 |
| TPV05 | PEP5 | PEP2 | PEP4 | PEP1 | PEP3 |
| TPV06 | PEP4 | PEP5 | PEP2 | PEP7* | PEP3 |
| TPV07 | PEP7* | PEP3 | PEP4 | PEP5 | PEP2 |
| TPV08 | PEP5 | PEP7* | PEP3 | PEP4 | PEP2 |
| TPV09 | PEP6 | PEP1 | PEP4 | PEP5 | PEP2 |
| TPV10 | PEP6 | PEP5 | PEP1 | PEP4 | PEP2 |
| TPV11 | PEP4 | PEP5 | PEP1 | PEP6 | PEP3 |
| TPV12 | PEP7* | PEP2 | PEP4 | PEP5 | PEP3 |
| TPV13 | PEP4 | PEP2 | PEP7* | PEP5 | PEP3 |
| TPV14 | PEP7* | PEP2 | PEP5 | PEP4 | PEP3 |
| TPV15 | PEP5 | PEP2 | PEP7* | PEP4 | PEP3 |
| TPV16 | PEP5 | PEP2 | PEP4 | PEP3 | PEP7* |
| TPV18 | PEP7* | PEP2 | PEP5 | PEP3 | PEP4 |

| | |
|---|---|
| $p > 0.05$ | |
| $p < 0.05, 10 \leq \Delta < 100$ | ▨ |
| $p < 0.05, 100 \leq \Delta < 200$ | ▧ |
| $p < 0.05, 200 \leq \Delta$ | ■ |

Fig. 2

| | Epitope specific IgG (fold induction vs. IFA) | | | | |
|---|---|---|---|---|---|
| Mixture administration | PEP2 | PEP3 | PEP4 | PEP5 | PEP7 |
| Peptide | N terminus | | | | C terminus |
| TPV01 | PEP5 | PEP2 | PEP4 | PEP7 | PEP3 |
| TPV02 | PEP5 | PEP2 | PEP7 | PEP3 | PEP4 |
| TPV03 | PEP4 | PEP6 | PEP5 | PEP7 | PEP3 |
| TPV04 | PEP5 | PEP2 | PEP4 | PEP6 | PEP3 |
| TPV05 | PEP5 | PEP2 | PEP4 | PEP1 | PEP3 |
| TPV06 | PEP4 | PEP5 | PEP2 | PEP7 | PEP3 |
| TPV07 | PEP7 | PEP3 | PEP4 | PEP5 | PEP2 |
| TPV08 | PEP5 | PEP7 | PEP3 | PEP4 | PEP2 |
| TPV09 | PEP6 | PEP1 | PEP4 | PEP5 | PEP2 |
| TPV10 | PEP6 | PEP5 | PEP1 | PEP4 | PEP2 |
| TPV11 | PEP4 | PEP5 | PEP1 | PEP6 | PEP3 |
| TPV12 | PEP7 | PEP2 | PEP4 | PEP5 | PEP3 |
| TPV13 | PEP4 | PEP2 | PEP7 | PEP5 | PEP3 |
| TPV14 | PEP7 | PEP2 | PEP5 | PEP4 | PEP3 |
| TPV15 | PEP5 | PEP2 | PEP7 | PEP4 | PEP3 |
| TPV16 | PEP5 | PEP2 | PEP4 | PEP3 | PEP7 |
| TPV17 | PEP2 | PEP3 | PEP4 | PEP5 | PEP7 |

| | |
|---|---|
| fold<2 | |
| 2≦fold<10 | |
| 10≦fold<100 | |
| 100≦fold | |

PEPTIDE HAVING 5 LINKED CTL EPITOPES

CROSS-REFERENCE TO RELATED APPLICATIONS

This application is a National Stage application of PCT/JP2014/055555, filed Mar. 5, 2014, which claims priority from Japanese application JP 2013-047271, filed Mar. 8, 2013.

TECHNICAL FIELD

The present invention relates to a novel peptide that is useful as a cancer antigen peptide. More particularly, the present invention relates to a novel cancer antigen peptide having 5 linked peptides capable of induction of HLA-A-restricted CTL responses and a pharmaceutical composition utilizing the same.

BACKGROUND ART

Cancer is the top cause of death in Japan. Approximately 350,000 patients die of cancer every year, and cancer is still a serious disease nowadays. The primary techniques for cancer treatment that have been established are surgical resection, anti-cancer drug treatment, and radiation treatment. However, such treatment strategies are problematic in terms of, for example, recurrence, decline in quality of life (QOL), and lack of treatment options in the case of advanced-stage cancers that cannot be treated with the strategies described above.

Cancer immunotherapy (cancer vaccines) has been expected as a novel therapeutic technique for a long period of time, and clinical studies on peptide vaccines for cancer treatment were initiated throughout the world in 1990 when epitope peptides in human tumor antigens became identifiable. According to the results of analysis of clinical studies conducted via administration of a peptide alone or in combination with other agents, however, the response rate is as low as 2.7% among 1,000 or more cases (Rosenberg S A et al., Nature Med., 2004, 10 (9): 909-15). Thus, difficulty in practical application has been pointed out.

Meanwhile, clinical studies involving the use of particular peptide vaccines for cancer treatment have been underway for a long period of time in Japan, and the achievements of such studies have gradually been articulated. In recent years, a strategy of administration of a multiple cancer peptides instead of a single type of cancer peptide has been attempted, with the aim of improving the outcome for treatment. For example, the HLA type and specific immune responses of a patient are examined in advance, so as to implement a tailor-made cancer treatment using peptide vaccines comprising selecting multiple adequate peptides to be administered, and safety and anti-tumor effects thereof have been verified. Through administration of tailor-made peptide vaccines alone or in combination with anti-cancer drugs, more specifically, excellent clinical effects and safety have been achieved in cases of brain tumor, uterine cervix cancer, prostate cancer, and pancreatic cancer (Terasaki, M. et al., J. Clin. Oncol., 2011, 29 (3): 337-44; Noguchi, M. et al., Cancer Immunol. Immunother., 2010, 59 (7): 1001-9; Yanagimoto, II. et al., Cancer Sci., 2007, 98 (4): 605-11).

The cell-mediated immunity consisting of epitope specific cytotoxic T lymphocytes (hereafter, abbreviated as "CTL"), which are considered to be major effector cells in cancer treatment using peptide vaccines, is HLA-restrictive. Accordingly, development of peptide vaccines for cancer treatment exclusively targeting patients with a particular HLA type, and specifically an HLA-A2 or HLA-A24 type, has been attempted because of the large number of patients therewith.

However, Japanese people with such two HLA types account for approximately 40% and 60%, respectively (Sette, A. et al., Immunogenetics, 1999, 50 (3-4): 201-12). Disadvantageously, patients with other HLA types cannot gain benefits from peptide vaccines for cancer treatment. In addition, the time of initiation of treatment would be postponed because of HLA typing performed prior to the initiation of treatment, and it would increase the burden on patients. Accordingly, research and development of peptide vaccines for cancer treatment that are applicable to all cancer patients without HLA typing are desired.

Regarding cancer treatment using peptide vaccines, in addition to activations of CTLs for cell-mediated immunity, inductions of production of immunoglobulins known as the humoral immunity is known to be attributable to survival benefit (Noguchi, M. et al., Cancer Biol. Ther., 2011, 10 (12):1266-79).

SUMMARY OF THE INVENTION

Objects to be Attained by the Invention

An object of the present invention is to provide a cancer antigen peptide that can be administered as a peptide vaccine for cancer to a wide range of cancer patients without the need for HLA typing and regardless of the HLA types of patients.

Means for Attaining the Objects

The present inventors have conducted concentrated studies in order to attain the above objects. As a result, they discovered that a peptide having 5 linked CTL epitopes obtained by linking 5 peptides via linkers selected from among CTL epitope peptides reported to be capable of induction of HLA-A2, HLA-A24, HLA-A26, or HLA-A3 supertype-restricted CTL response or a plurality of HLA-A-restricted CTL responses could be administered to a wide range of cancer patients without the need for HLA typing and regardless of the HLA types of patients. They also discovered that administration of such peptide having 5 linked CTL epitopes could strongly induce CTLs and immunoglobulins specific for CTL epitope peptides composing such peptide. This has led to the completion of the present invention.

Specifically, the present invention has the following features.

[1] A peptide having 5 linked epitopes, wherein the 5 epitopes are selected, optionally redundantly, from the group consisting of CTL epitope peptides: the peptide as shown in SEQ ID NO: 1 (PEP1); the peptide as shown in SEQ ID NO: 2 (PEP2); the peptide as shown in SEQ ID NO: 3 (PEP3); the peptide as shown in SEQ ID NO: 4 (PEP4); the peptide as shown in SEQ ID NO: 5 (PEP5); the peptide as shown in SEQ ID NO: 6 (PEP6); and the peptide as shown in SEQ ID NO: 7 (PEP7); linked via linkers, and the peptide having 5 linked epitopes has one or more features selected from the features (1) to (12) below:

(1) the peptide comprises a sequence composed of PEP5 and PEP2 successively disposed in such order from the N terminus via a linker;

(2) the peptide comprises a sequence composed of PEP2 and PEP4 successively disposed in such order from the N terminus via a linker;

(3) the peptide comprises a sequence composed of PEP4 and PEP6 successively disposed in such order from the N terminus via a linker;

(4) the peptide comprises a sequence composed of PEP6 and PEP3 successively disposed in such order from the N terminus via a linker;

(5) the peptide comprises a sequence composed of PEP4 and PEP1 successively disposed in such order from the N terminus via a linker;

(6) the peptide comprises a sequence composed of PEP1 and PEP3 successively disposed in such order from the N terminus via a linker;

(7) the peptide comprises a sequence composed of PEP4 and PEP2 successively disposed in such order from the N terminus via a linker;

(8) the peptide comprises a sequence composed of PEP1 and PEP4 successively disposed in such order from the N terminus via a linker;

(9) the peptide comprises a sequence composed of PEP5 and PEP1 successively disposed in such order from the N terminus via a linker;

(10) the peptide comprises a sequence composed of PEP6 and PEP5 successively disposed in such order from the N terminus via a linker;

(11) the peptide comprises PEP2 at the C terminus; and

(12) the peptide comprises PEP3 at the C terminus.

[2] The peptide having 5 linked epitopes according to [1], which comprises a sequence at the N terminus composed of PEP5 and PEP2, PEP6 and PEP5, or PEP4 and PEP6 successively disposed in such order from the N terminus via a linker and/or a sequence at the C terminus composed of PEP7 and PEP3, PEP4 and PEP3, PEP6 and PEP3, PEP1 and PEP3, PEP5 and PEP2, PEP4 and PEP2, or PEP5 and PEP3 successively disposed in such order from the N terminus via a linker.

[3] The peptide having 5 linked epitopes according to [2], which comprises a sequence selected from the sequences (a) to (p) below:

(a) PEP5-PEP2-PEP4-PEP7-PEP3;
(b) PEP5-PEP2-PEP7-PEP3-PEP4;
(c) PEP4-PEP6-PEP5-PEP7-PEP3;
(d) PEP5-PEP2-PEP4-PEP6-PEP3;
(e) PEP5-PEP2-PEP4-PEP1-PEP3;
(f) PEP4-PEP5-PEP2-PEP7-PEP3;
(g) PEP7-PEP3-PEP4-PEP5-PEP2;
(h) PEP5-PEP7-PEP3-PEP4-PEP2;
(i) PEP6-PEP1-PEP4-PEP5-PEP2;
(j) PEP6-PEP5-PEP1-PEP4-PEP2;
(k) PEP4-PEP5-PEP1-PEP6-PEP3;
(l) PEP7-PEP2-PEP4-PEP5-PEP3;
(m) PEP4-PEP2-PEP7-PEP5-PEP3;
(n) PEP7-PEP2-PEP5-PEP4-PEP3;
(o) PEP5-PEP2-PEP7-PEP4-PEP3; or
(p) PEP5-PEP2-PEP4-PEP3-PEP7,
wherein "-" represents a linker.

[4] The peptide having 5 linked epitopes according to any of [1] to [3], wherein the linker is an amino acid linker.

[5] The peptide having 5 linked epitopes according to [4], wherein the amino acid linker is an arginine dimer composed of two arginine residues linked to each other.

[6] A CTL obtained by stimulating peripheral blood lymphocytes using the peptide having 5 linked epitopes according to any of [1] to [5].

[7] A pharmaceutical composition used for treatment or prevention of cancer comprising, as an active ingredient, the peptide having 5 linked epitopes according to any of [1] to [5] or the CTL according to [6].

[8] The pharmaceutical composition according to [7], which is an immunotherapeutic agent.

[9] A method for treatment of cancer comprising administering the peptide having 5 linked epitopes according to any of [1] to [5] or the CTL according to [6] to a cancer patient.

[10] A method for immunizing a subject against cancer comprising administering the peptide having 5 linked epitopes according to any of [1] to [5] or the CTL according to [6] to a subject.

This description includes part or all of the content as disclosed in the description and/or drawings of Japanese Patent Application No. 2013-047271, which is a priority document of the present application.

Effects of the Invention

The present invention can provide a cancer antigen peptide that can be administered to a wide range of cancer patients as a peptide vaccine for cancer without the need for HLA typing and regardless of the HLA types of patients.

The peptide having 5 linked CTL epitopes according to the present invention can be administered to a wide range of cancer patients without the need for HLA typing. Examples of such patients include those who are HLA-A2 positive patients, HLA-A24 positive patients, HLA-A26 positive patients, and HLA-A3 supertype positive patients. The peptide as described above can be used for treatment and/or prevention of cancer or diseases caused thereby of such patients. In addition, expression of the tumor antigens constituting the peptide having 5 linked CTL epitopes according to the present invention is observed in a plurality of types of cancers. Accordingly, the peptide having 5 linked CTL epitopes according to the present invention can be used as a pharmaceutical composition (and more specifically, as an immunotherapeutic agent) for treatment or prevention of a variety of cancers. Through administration of the peptide having 5 linked CTL epitopes according to the present invention, further, CTL epitope peptide specific CTLs and immunoglobulins can be induced more strongly, in comparison with administration of a mixture of an equivalent amount of CTL epitope peptides, and antitumor immunity can be more efficiently activated.

BRIEF DESCRIPTION OF THE DRAWINGS

FIG. 1 shows the results of epitope specific CTL induction in mouse models to which the peptide having 5 linked epitopes has been administered (*: unexamined).

FIG. 2 shows the results of assay of the epitope specific IgG antibody titer in sera of mouse models to which the peptide having 5 linked epitopes has been administered.

EMBODIMENTS FOR CARRYING OUT THE INVENTION

Hereafter, the present invention is described in greater detail.

1. Peptide Having 5 Linked Epitopes

In the present invention, the "peptide having 5 linked epitopes" means 5 peptides selected from among CTL epitope peptides derived from the same and/or different tumor antigen molecules linearly linked via linkers as a single molecule.

The "CTL epitope peptide derived from tumor antigen molecules" is a peptide resulting from decomposition of tumor antigens within tumor cells, and it is bound to the HLA class I molecule and presented on the cell surface. Thus, it is recognized by a tumor-specific CTL and/or it can induce and/or activate tumor-specific CTLs. "Induction of tumor-specific CTLs" refers to differentiation and/or proliferation of CTLs that specifically recognize CTL epitope peptides derived from tumor antigen molecules in vitro or in vivo. Further, "activation of tumor-specific CTL" refers to production of interferon-γ (IFN-γ) when CTL recognizes an antigen presented by the HLA class I molecule. The "CTL epitope peptide derived from a tumor antigen molecule" used herein is occasionally referred to as a "CTL epitope peptide."

Known peptides can be used as the CTL epitope peptides according to the present invention, and examples thereof include the following:

```
PEP1:  KLVERLGAA
       (SEQ ID NO: 1 [WO 01/011044]);

PEP2:  ASLDSDPWV
       (SEQ ID NO: 2 [WO 02/010369]);

PEP3:  LLQAEAPRL
       (SEQ ID NO: 3 [WO 00/12701]);

PEP4:  DYSARWNEI
       (SEQ ID NO: 4 [JP H11-318455 A (1999)]);

PEP5:  VYDYNCHVDL
       (SEQ ID NO: 5 [WO 00/12701]);

PEP6:  LYAWEPSFL
       (SEQ ID NO: 6 [JP 2003-000270 A]);

PEP7:  QIRPIFSNR
       (SEQ ID NO: 7 [Cancer Immunol. lmmunother.,
       2007, 56 (5), 689-698]).
```

In this description, the peptide as shown in SEQ ID NO: 1, the peptide as shown in SEQ ID NO: 2, the peptide as shown in SEQ ID NO: 3, the peptide as shown in SEQ ID NO: 4, the peptide as shown in SEQ ID NO: 5, the peptide as shown in SEQ ID NO: 6, and the peptide as shown in SEQ ID NO: 7 are occasionally referred to as "PEP1," "PEP2," "PEP3," "PEP4," "PEP5," "PEP6," and "PEP7," respectively.

In the present invention, a peptide having an amino acid sequence having substitution, insertion, deletion, and/or addition of one or a plurality of amino acids in the amino acid sequence of PEP1, PEP2, PEP3, PEP4, PEP5, PEP6, or PEP7 and having the capacity for inducing CTL and the capacity for inducting immunoglobulin productions equivalent to or higher than those of the original peptide can be used as a "CTL epitope peptide." The term "plurality" used herein refers to 1 to 3, and preferably 1 or 2. An example of such peptide is a peptide obtained by substitution of amino acids having properties similar to those of the original amino acid (i.e., a peptide obtained by conservative amino acid substitution).

PEP1 PEP2, PEP3, PEP4, and PEP5 are captured by the HLA-A2, PEP2, PEP4, PEP5, and PEP6 are captured by the HLA-A24, PEP2, PEP4, PEP5, and PEP7 are captured by the HLA-A3 supertype, PEP2 and PEP5 are captured by the HLA-A26, and CTLs can then be induced and/or activated. Expression of genes encoding such CTL epitope peptides is observed in a plurality of types of cancers (Yang, D. et al., Cancer Res., 1999, 59: 4056-63; Harashima, N. et al., Eur. J. Immunol., 2001, 31 (2), 323-32).

Five peptides selected, optionally redundantly, from among PEP1, PEP2, PEP3, PEP4, PEP5, PEP6, and PEP7 are linearly linked via linkers.

Any linker can be used, provided that it is cleaved upon administration of a peptide having 5 linked epitopes to an organism, and the linked CTL epitope peptides can be separated from each other. Examples thereof include an ester bond, an ether bond, an amino bond, a sugar chain linker, a polyethylene glycol linker, and an amino acid linker. Examples of amino acid sequences used as amino acid linkers include an arginine dimer, a lysine dimer, a glycine dimer, a glycine pentamer, a glycine hexamer, an alanine-alanine-tyrosine (AAY), isoleucine-leucine-alanine (ILA), and arginine-valine-lysine-arginine (RVKR), with an arginine dimer being preferable.

CTL epitope peptides to be selected and the arrangements thereof can be determined by administering a peptide having 5 linked epitopes obtained by synthesizing epitopes in given combinations and in a given order to human HLA-A transgenic mice and evaluating the occurrence of CTL epitope peptide specific CTL induction in vivo.

Preferably, the peptide having 5 linked epitopes according to the present invention has one or more features selected from the features (1) to (12) below:

(1) the peptide comprises a sequence composed of PEP5 and PEP2 successively disposed in such order from the N terminus via a linker;

(2) the peptide comprises a sequence composed of PEP2 and PEP4 successively disposed in such order from the N terminus via a linker;

(3) the peptide comprises a sequence composed of PEP4 and PEP6 successively disposed in such order from the N terminus via a linker;

(4) the peptide comprises a sequence composed of PEP6 and PEP3 successively disposed in such order from the N terminus via a linker;

(5) the peptide comprises a sequence composed of PEP4 and PEP1 successively disposed in such order from the N terminus via a linker;

(6) the peptide comprises a sequence composed of PEP1 and PEP3 successively disposed in such order from the N terminus via a linker;

(7) the peptide comprises a sequence composed of PEP4 and PEP2 successively disposed in such order from the N terminus via a linker;

(8) the peptide comprises a sequence composed of PEP1 and PEP4 successively disposed in such order from the N terminus via a linker;

(9) the peptide comprises a sequence composed of PEP5 and PEP1 successively disposed in such order from the N terminus via a linker;

(10) the peptide comprises a sequence composed of PEP6 and PEP5 successively disposed in such order from the N terminus via a linker;

(11) the peptide comprises PEP2 at the C terminus; and

(12) the peptide comprises PEP3 at the C terminus.

Preferably, the peptide having 5 linked epitopes according to the present invention comprises: (I) a sequence composed of PEP5 and PEP2, PEP6 and PEP5, or PEP4 and PEP6 successively disposed in such order from the N terminus via a linker at the N terminus; and/or (II) a sequence composed of PEP7 and PEP3, PEP4 and PEP3, PEP6 and PEP3, PEP1 and PEP3, PEP5 and PEP2, PEP4 and PEP2, or PEP5 and PEP3 successively disposed in such order from the N terminus via a linker at the C terminus.

More preferably, the peptide having 5 linked epitopes according to the present invention comprises or consists of a sequence selected from among the sequences (a) to (p) below, wherein "-" represents a linker:

(a) PEP5-PEP2-PEP4-PEP7-PEP3;
(b) PEP5-PEP2-PEP7-PEP3-PEP4;
(c) PEP4-PEP6-PEP5-PEP7-PEP3;
(d) PEP5-PEP2-PEP4-PEP6-PEP3;
(e) PEP5-PEP2-PEP4-PEP1-PEP3;
(f) PEP4-PEP5-PEP2-PEP7-PEP3;
(g) PEP7-PEP3-PEP4-PEP5-PEP2;
(h) PEP5-PEP7-PEP3-PEP4-PEP2;
(i) PEP6-PEP1-PEP4-PEP5-PEP2;
(j) PEP6-PEP5-PEP1-PEP4-PEP2;
(k) PEP4-PEP5-PEP1-PEP6-PEP3;
(l) PEP7-PEP2-PEP4-PEP5-PEP3;
(m) PEP4-PEP2-PEP7-PEP5-PEP3;
(n) PEP7-PEP2-PEP5-PEP4-PEP3;
(o) PEP5-PEP2-PEP7-PEP4-PEP3; or
(p) PEP5-PEP2-PEP4-PEP3-PEP7.

In the peptide having 5 linked epitopes according to the present invention, a CTL epitope peptide specific CTLs can be induced and/or activated and immunoglobulins specific for a relevant CTL epitope peptide can be induced in preferably two types, more preferably three types, further preferably 4 types, and most preferably 5 types of CTL epitope peptides of the 5 linked types of CTL epitope peptides. In the present invention, the term "immunoglobulins" refers to IgG, IgM, IgA, or IgD.

2. Production of a Peptide Having 5 Linked Epitopes

The peptide having 5 linked epitopes according to the present invention can be produced by common techniques, for example, peptide synthesis, such as liquid-phase synthesis or solid-phase synthesis, or peptide synthesis involving the use of an automated peptide synthesizer (Kelley et al., Genetics Engineering Principles and Methods, Setlow, J. K. eds., Plenum Press NY., 1990, Vol. 12, pp. 1-19; Stewart et al., Solid-Phase Peptide Synthesis, 1989, W. H. Freeman Co.; Houghten, Proc. Natl. Acad. Sci., U.S.A., 1985, 82: p. 5132, "Shin Seikagaku Jikken Kouza (New Biochemical Experiment) 1, Protein IV, 1992, the Japanese Biochemical Society (ed.), Tokyo Kagaku Doujin). Peptide synthesis is carried out by preparing amino acids in which functional groups other than α-amino groups and α-carboxyl groups to be bound of the amino acids are protected and forming peptide bonds between α-amino groups and α-carboxyl groups of the amino acids. In general, a carboxyl group of an amino acid residue located at the C terminus of a peptide is bound to a solid phase via an adequate spacer or linker. A protective group at the amino terminus of the dipeptide obtained above is selectively removed and a peptide bond is formed between the amino terminus and the α-carboxyl group of the subsequent amino acid residue. This procedure is continued to produce a peptide with a protected side group, and all protective groups are removed and separated from the solid phase at the end. Protective group types, methods for protecting the same, and methods of peptide binding are described in detail in the documents mentioned above.

Alternatively, a peptide may be produced via genetic recombination with the use of a nucleic acid encoding the peptide having 5 linked epitopes according to the present invention, phage display, or other techniques.

A genetic recombination technique comprises inserting DNA encoding the peptide having 5 linked epitopes according to the present invention into an adequate expression vector, introducing the vector into adequate host cells, culturing the cells, and recovering the target peptides from the cells or the extracellular fluid. Examples of vectors include, but are not limited to, plasmid, phage, cosmid, phagemid, and virus vectors. Vectors are introduced into host cells, such as bacterial host cells (e.g., *E. coli* and *Bacillus subtilis*), yeast cells, insect cells, animal cells (e.g., mammalian cells), and plant cells. Transformation or transfection into such cells is carried out via, for example, the calcium phosphate method, electroporation, lipofection, the particle gun method, or the PEG method. Transformed cells are cultured in accordance with a conventional technique for host organism culture. In order to facilitate recovery of the peptide according to the present invention, it is preferable that a peptide generated via expression be secreted extracellularly. To this end, DNA encoding a peptide sequence that enables peptide secretion from the cells is bound to the 5' terminal side of DNA encoding a target peptide. Alternatively, a target peptide accumulated in the cells can be recovered. In such a case, cells are physically or chemically broken and a target peptide is recovered via a protein purification technique.

The peptide thus obtained can be recovered or purified via a conventional technique, for example, chromatography techniques, such as gel filtration chromatography, ion exchange column chromatography, affinity chromatography, reverse phase column chromatography, or HPLC, ammonium sulfate fractionation, ultrafiltration, or immunoadsorption.

3. Cytotoxic T Lymphocytes

With the use of the peptide having 5 linked epitopes according to the present invention, CTL epitope peptide specific CTLs that damage cancer cells can be obtained in vitro. A method for inducing CTL using a CTL epitope peptide in vitro is known (e.g., JP 2006-14637 A), and such technique can be employed in the present invention. For example, plate adhesion cells in the peripheral blood mononuclear cells (PBMCs) derived from healthy individuals or cancer patients are cultured in the presence of cytokines, such as GM-CSF or IL-4 so as to induce dendritic cells (DCs). After the dendritic cells have been pulsed with the peptide having 5 linked epitopes according to the present invention, x-rays are applied thereto, so as to prepare antigen-presenting cells (stimulators). When DCs cannot be used, the peripheral blood mononuclear cells (PBMCs) derived from healthy individuals or the same cancer patients may be pulsed with the peptide having 5 linked epitopes according to the present invention, x-rays may be applied thereto, and the resultants may be used. Subsequently, peripheral blood mononuclear cells (PBMCs) derived from healthy individuals or peripheral blood mononuclear cells (PBMCs) or lymphocytes in the relevant lymph nodes (i.e., responders) derived from cancer patients are added and then cultured in the presence of cytokines, such as IL-2, IL-4, or IL-7. Thereafter, the antigen presenting cells obtained via pulsing described above are stimulated again with the addition of the peptide having 5 linked epitopes according to the present invention and further cultured in the presence of cytokines, such as IL-2.

Any medium in which T lymphocytes can survive may be used as a cell culture medium used for CTL induction. For example, a medium prepared by adding various cytokines (e.g., IL-2) and fetal calf serum (FCS) to RHAMα medium (LAK medium described in Kawai, K., Sasaki, T., Saijo-Kurita, K., Akaza, H., Koiso, K., and Ohno, T., Cancer Immunol. Immunother., 35, 225-229, 1992), AIMV medium (GIBCO BRL, Life Technologies, INC.), or RPMI 1640 medium can be used.

Culture may be conducted under conditions well known in the art. For example, culture temperature is at 33° C. to 41° C., and preferably 37° C. An inert gas containing air or oxygen of adequate concentration and carbon dioxide of adequate concentration (e.g., 5% $CO_2$) to adjust the pH of the medium to about 7.4 can be used as a gas phase. Culture is preferably conducted for 4 to 10 days, and more preferably 7 days. Some CTLs induced via such culture are CTL epitope peptide specific for preferably two types, more preferably three types, further preferably four types, and most preferably five types of CTL epitope peptides among the five types of CTL epitope peptides constituting the peptide having 5 linked epitopes, and thus they can specifically damage cancer cells.

4. Pharmaceutical Composition

The peptide having 5 linked epitopes according to the present invention can be used as an active ingredient of a pharmaceutical composition used for cancer immunotherapy.

The pharmaceutical composition according to the present invention can contain, as an active ingredient(s), one or more of the peptides having 5 linked epitopes. Thus, stronger effects can be expected by including a plurality of the peptides having 5 linked epitopes.

Genes encoding PEP1, PEP2, PEP3, PEP4, PEP5, PEP6, and PEP7 included in the peptide having 5 linked epitopes according to the present invention are observed to be expressed in a plurality of types of solid cancers and blood cancers. Examples of solid cancers include brain tumor, lung cancer, breast cancer, thyroid cancer, uterine cervix cancer, cancer of uterine body, ovarian cancer, esophageal cancer, gastric cancer, GIST, pancreatic cancer, colon cancer, rectal cancer, anal cancer, renal cancer, liver cancer, biliary tract cancer, head and neck cancer, bladder cancer, prostate cancer, malignant melanoma, skin cancer, lingual cancer, osteosarcoma, chondrosarcoma, fibrosarcoma, liposarcoma, angiosarcoma, rhabdomyoblastoma, and leiomyosarcoma. Examples of blood cancers include leukemia, malignant lymphoma, and myeloma. Accordingly, the peptide having 5 linked epitopes according to the present invention is useful for the treatment or prevention of such cancers. The term "treatment or prevention of cancer" used herein refers to prevention of the development/recurrence of cancer, suppression of the progression/exacerbation of cancer, or the improvement of cancer conditions.

The pharmaceutical composition according to the present invention can contain pharmaceutically acceptable materials, such as various common organic or inorganic carriers. Examples of pharmaceutical carriers that can be used include stabilizers, antibacterials, buffers, isotonizing agents, chelating agents, pH adjusters, surfactants, fillers, thickeners, binders, humectants, disintegrators, surface active agents, lubricants, soothing agents, diluents, and excipients that are generally used in accordance with the form of administration of relevant pharmaceutical preparations. Pharmaceutical preparations are preferably prepared in the form of formulations supplemented with such carriers in accordance with conventional techniques.

The pharmaceutical composition according to the present invention can contain an adjuvant that is known to be used at the time of vaccine administration. Examples of adjuvants include Complete Freund's adjuvant (CFA), Incomplete Freund's adjuvant (IFA), alum, lipid A, monophosphoryl lipid A, bacterial preparations such as BCG (*Bacillus-Calmette-Guerrin*), preparations of bacterial components such as tuberculin, naturally-occurring polymers, such as keyhole limpet hemocyanin and yeast mannan, muramyl-tripeptide, muramyl-dipeptide, or a derivative of either thereof, alum, and nonionic block copolymers. These adjuvants can be used alone or in combinations of two or more. Adjuvants may be administered simultaneously with the pharmaceutical composition according to the present invention in the form of a mixture or as an emulsion.

In addition to the peptide having 5 linked epitopes, the pharmaceutical composition according to the present invention may comprise one or more of a known CTL epitope peptide derived from tumor antigen molecules, a peptide containing the same, or a peptide comprising the CTL epitope peptides linked to each other (hereafter, referred to as "known CTL epitope peptides derived from tumor antigen molecules"). Examples of known CTL epitope peptides derived from tumor antigen molecules include, but are not limited to, WT-1 p126-134, modified (M236Y) WT-1 p235-243, NY-ESO-1 p157-165, modified (T210M) gp100 p209-217, survivin-2B p80-88, Her-2/neu p63-71, VEGFR2 p169-177, MART-1 p26-35, Glypican-3 p298-306, and SPARC p143-151. In this case, the peptide having 5 linked epitopes according to the present invention and the known CTL epitope peptides derived from tumor antigen molecules may be prepared in the form of a single-agent preparation. Alternatively, a preparation comprising, as an active ingredient, the peptide having 5 linked epitopes according to the present invention may be separated from a preparation comprising, as an active ingredient, the known CTL epitope peptides derived from tumor antigen molecules.

The dosage form of the pharmaceutical composition according to the present invention can be selected in accordance with the form of administration. Representative examples of dosage forms include, but are not limited to, liquid preparations, emulsions, liposome preparations, lipid emulsions, cyclodextrin inclusion complexes, suspensions, ointments, creams, transdermally absorbed agents, transmucosally absorbed agents, tablets, pills, capsules, powders, powdered drugs, granules, fine grains, and syrups. In accordance with the route of administration, such dosage forms are further classified as, for example, oral preparations, parenteral preparations, transnasal preparations, transvaginal preparations, suppositories, sublingual formulations, inhalants, eye drops, or ear drops, and such preparations can be combined, molded, or prepared in accordance with conventional techniques. In addition to the application in the form of liquid preparations, such preparation can be subjected to lyophilization, so as to make the pharmaceutical preparation storable. When such pharmaceutical preparation is to be used, it may be dissolved with the aid of, for example, a buffer containing water and physiological saline, so as to adjust the concentration thereof to an adequate level.

The pharmaceutical composition according to the present invention may comprise, as an active ingredient, CTLs induced in vitro with the use of the peptide having 5 linked epitopes according to the present invention. Such pharmaceutical composition is preferably in the form of a parenteral agent.

5. Treatment Method

The pharmaceutical composition according to the present invention can be administered to a wide range of cancer patients, such as patients who are positive for HLA types selected from the group consisting of HLA-A2, HLA-A24, HLA-A26, and HLA-A3 supertype, and treatment can be initiated without conducting HLA typing prior to the treatment.

When the pharmaceutical composition according to the present invention is administered to a cancer patient, CTLs specific for two or more, preferably 3 or more, more preferably 4 or more, and further preferably 5 or more types of CTL epitope peptides constituting the peptide having 5 linked epitopes as an active ingredient of the pharmaceutical composition can be induced and/or activated. In addition, production of immunoglobulins specific for relevant CTL epitope peptides can be induced. The level of induction of immunoglobulin production upon administration of the peptide having 5 linked epitopes as an active ingredient is significantly higher than the level of induction of immunoglobulin production observed upon administration of a mixture of CTL epitope peptides that are to be contained in the peptide having 5 linked epitopes but are not linked to each other. Accordingly, the peptide having 5 linked epitopes according to the present invention can effectively treat or prevent cancer in a cancer patient.

The pharmaceutical composition according to the present invention can be administered via, for example, oral administration, intravenous administration, intraarterial administration, intramuscular administration, subcutaneous administration, intracutaneous administration, sublingual administration, intraperitoneal administration, intrarectal administration, transdermal administration, transmucosal administration, transnasal administration, transvaginal administration, transocular administration, or aspiration. When preparations comprising, as active ingredients, a plurality of peptides having 5 linked epitopes or known CTL epitope peptides derived from tumor antigen molecules are prepared in the form of separate pharmaceutical compositions, such pharmaceutical compositions can be administered simultaneously or non-simultaneously via the same route or via separate routes.

Dosage of the pharmaceutical composition according to the present invention can be adequately adjusted in accordance with factors such as the conditions/severity of cancer to be treated, the age of the patient, or the body weight of the patient. For example, a pharmaceutical composition containing the peptide having 5 linked epitopes in an amount of 0.0001 mg to 1000 mg, preferably 0.001 mg to 100 mg, and further preferably 0.01 mg to 50 mg may be repeatedly administered once every several days, several weeks, or several months. When the pharmaceutical composition according to the present invention comprises, as active ingredients, CTLs induced in vitro with the use of the peptide having 5 linked epitopes according to the present invention, it is preferable that $2 \times 10^6$ to $2 \times 10^8$ CLTs be administered per kg of the body weight every day at intervals of 1 to 2 weeks.

The pharmaceutical composition according to the present invention can be administered to a cancer patient in combination with pharmaceutical products that are generally used for cancer chemotherapy. Examples of such pharmaceutical products include: alkylating agents, such as cyclophosphamide, temozolomide, and bendamustine; antimetabolites, such as tegafur-uracil, tegafur-gimeracil-oteracil potassium, methotrexate, and gemcitabine; platinum-containing drugs, such as cisplatin and oxaliplatin; plant alkaloid preparations, such as irinotecan, eribulin, paclitaxel, docetaxel, and vincristine; carcinostatic antibiotics, such as doxorubicin, bleomycin, and actinomycin D; molecular-targeted drugs, such as imatinib, sunitinib, gefitinib, sorafenib, everolimus, trastuzumab, bevacizumab, rituximab, cetuximab, panitumumab, and mogamulizumab; and hormonal therapy agents, such as bicalutamide, estramustine, and exemestane. Such pharmaceutical products can be administered simultaneously or non-simultaneously with the pharmaceutical composition according to the present invention via the same route or via separate routes.

Hereafter, the present invention is described in greater detail with reference to the examples, although the present invention is not limited to these examples.

EXAMPLES

Example 1

Peptide Synthesis and Purification

The CTL epitope peptides and the peptides having 5 linked epitopes were synthesized using a commercially available peptide synthesizer (Prelude, Protein Technologies, Inc.) by the solid-phase synthesis (Fmoc) method. The resulting various synthetic peptides were purified using the YMC-Pack Pro C18 column (YMC Co., Ltd.) and the HPLC system (Gilson), lyophilized, stored at cool temperature in the dark, and then provided to the examples described below.

Table 1 shows the amino acid sequences of the synthesized CTL epitope peptides and Table 2 shows the amino acid sequences of the peptides having 5 linked epitopes.

WT1 (SEQ ID NO: 8) was synthesized as a control peptide to be bound to HLA-A2 and Her2 (SEQ ID NO: 9) was synthesized as a control peptide to be bound to HLA-A24.

TABLE 1

CTL epitope peptides

| Peptide | Origin | Amino acid sequence | SEQ ID NO: |
|---------|--------|---------------------|------------|
| PEP1 | Lck-246 | KLVERLGAA | SEQ ID NO: 1 |
| PEP2 | WHSC2-103 | ASLDSDPWV | SEQ ID NO: 2 |
| PEP3 | SART3-302 | LLQAEAPRL | SEQ ID NO: 3 |
| PEP4 | SART2-93 | DYSARWNEI | SEQ ID NO: 4 |
| PEP5 | SART3-109 | VYDYNCHVDL | SEQ ID NO: 5 |
| PEP6 | MRP3-503 | LYAWEPSFL | SEQ ID NO: 6 |
| PEP7 | SART3-734 | QIRPIFSNR | SEQ ID NO: 7 |
| WT1 | WT1-126 | RMFPNAPYL | SEQ ID NO: 8 |
| Her2 | Her2-63 | TYLPTNASL | SEQ ID NO: 9 |

TABLE 2

Peptides having 5 linked epitopes

| Peptide | Amino acid sequence | SEQ ID NO: |
|---------|---------------------|------------|
| TPV01 | PEP5-RR-PEP2-RR-PEP4-RR-PEP7-RR-PEP3 | SEQ ID NO: 10 |

TABLE 2-continued

Peptides having 5 linked epitopes

| Peptide | Amino acid sequence | SEQ ID NO: |
|---|---|---|
| TPV02 | PEP5-RR-PEP2-RR-PEP7-RR-PEP3-RR-PEP4 | SEQ ID NO: 11 |
| TPV03 | PEP4-RR-PEP6-RR-PEP5-RR-PEP7-RR-PEP3 | SEQ ID NO: 12 |
| TPV04 | PEP5-RR-PEP2-RR-PEP4-RR-PEP6-RR-PEP3 | SEQ ID NO: 13 |
| TPV05 | PEP5-RR-PEP2-RR-PEP4-RR-PEP1-RR-PEP3 | SEQ ID NO: 14 |
| TPV06 | PEP4-RR-PEP5-RR-PEP2-RR-PEP7-RR-PEP3 | SEQ ID NO: 15 |
| TPV07 | PEP7-RR-PEP3-RR-PEP4-RR-PEP5-RR-PEP2 | SEQ ID NO: 16 |
| TPV08 | PEP5-RR-PEP7-RR-PEP3-RR-PEP4-RR-PEP2 | SEQ ID NO: 17 |
| TPV09 | PEP6-RR-PEP1-RR-PEP4-RR-PEP5-RR-PEP2 | SEQ ID NO: 18 |
| TFV10 | PEP6-RR-PEP5-RR-PEP1-RR-PEP4-RR-PEP2 | SEQ ID NO: 19 |
| TPV11 | PEP4-RR-PEP5-RR-PEP1-RR-PEP6-RR-PEP3 | SEQ ID NO: 20 |
| TPV12 | PEP7-RR-PEP2-RR-PEP4-RR-PEP5-RR-PEP3 | SEQ ID NO: 21 |
| TPV13 | PEP4-RR-PEP2-RR-PEP7-RR-PEP5-RR-PEP3 | SEQ ID NO: 22 |
| TPV14 | PEP7-RR-PEP2-RR-PEP5-RR-PEP4-RR-PEP3 | SEQ ID NO: 23 |
| TPV15 | PEP5-RR-PEP2-RR-PEP7-RR-PEP4-RR-PEP3 | SEQ ID NO: 24 |
| TPV16 | PEP5-RR-PEP2-RR-PEP4-RR-PEP3-RR-PEP7 | SEQ ID NO: 25 |
| TPV17 | PEP2-RR-PEP3-RR-PEP4-RR-PEP5-RR-PEP7 | SEQ ID NO: 26 |
| TPV18 | PEP7-RR-PEP2-RR-PEP5-RR-PEP3-RR-PEP4 | SEQ ID NO: 27 |

"-RR-" represents an arginine dimer.

Example 2

Inductions of Epitope Peptide Specific CTLs in Mouse Model and Detection of CTLs Using ELISPOT The peptides having 5 linked epitopes were dissolved in Otsuka distilled water (Otsuka Pharmaceutical Factory Inc.) at 2 mg/ml or 4 mg/ml, and the resulting solution was filled into the B Braun Injekt syringe. After the equivalent amount of Incomplete Freund's adjuvant (IFA) was filled into another syringe, these syringes were connected to each other using a GP syringe connector, and a solution of the peptides having 5 linked epitopes was thoroughly mixed with IFA to prepare an emulsion. The emulsion was weekly administered in amounts of 100 µl each in the vicinity of base of tail of mice (HLA-A2.1 transgenic and HLA-A24 transgenic mice (Taconic)), and administrations were carried out twice in total. Inguinal lymph nodes were corrected from mice 1 week after the final administration. A lymph node cell suspension was adjusted to $5 \times 10^6$ cells/ml using Complete Medium (RPMI-1640, 10% heat-inactivated FBS, 100 U/ml penicillin, 100 µg/ml streptomycin, and 50 µM 2-mercaptoethanol), the target CTL epitope peptide (final concentration: 10 µg/ml), recombinant mouse IL-15 (final concentration: 100 ng/ml), and recombinant mouse IL-21 (final concentration: 100 ng/ml) were added, these cells were plated onto a 24-well plate at 1 ml/well, and were cultured in an incubator at 37° C. in the presence of 5% $CO_2$ for 8 days. Thereafter, the cells were collected and plated on an anti-IFN-γ antibody-immobilized plate included in the Murine IFN-γ ELISpot Kit (GEN-PROBE) at $1 \times 10^5$ cells/well. Subsequently, splenocytes obtained from the spleen of syngeneic mouse and irradiated with 30-Gy X-rays were plated on the same plate at $1 \times 10^5$ cells/well as antigen presenting cells, the target CTL epitope peptide or the negative control peptide (final concentration: 10 µg/ml) were added, and incubation was carried out in an incubator at 37° C. in the presence of 5% $CO_2$ overnight. On the following day, IFN-γ-producing cell spots were colored according to manufacturer's instructions. The number of IFN-γ-producing cell spots was quantified using an ELISPOT analyzer (Immunospot S6, Cellular Technology Ltd.). Induction of CTL epitope peptide specific CTL was evaluated as positive when the number of IFN-γ-producing cell spots in the wells supplemented with the target CTL epitope peptides was significantly higher than that observed in the wells supplemented with the negative control peptides (Student's t-test, $p<0.05$). WT1 or Her2 was used as the negative control peptide. In order to visualize the CTL induction level, the results of the following equation were designated as "Δ" (the average number of IFN-γ-producing cell spots in wells supplemented with the target CTL epitope peptides)−(the average number of IFN-γ-producing cell spots in wells supplemented with the negative control peptides). The results are represented as positive in case of $10 \leq \Delta < 100$; medium positive in case of $100 \leq \Delta < 200$; and strongly positive in case of $200 \leq \Delta$.

FIG. 1 shows the results of evaluation of CTL epitope peptide specific CTL induction. As shown in FIG. 1, a peptide having 5 linked epitopes comprising a PEP5-RR-PEP2 or PEP4-RR-PEP2 sequence or a peptide having 5 linked epitopes comprising PEP5 at the C terminus induced at least 3 types of CTLs. In contrast, there were no more than two CTLs induced by a peptide composed of 5 epitopes such as TPV18.

The above results demonstrate that administration of a peptide having 5 linked epitopes prepared by linking known CTL epitope peptides via arginine dimers to mice cannot always induce epitope specific CTLs specific for all CTL epitope peptides.

Example 3

Preparation of CTL Epitope Peptide-immobilized Beads

Peptides were immobilized onto xMAP Multi-Analyte COOH Microspheres (Luminex Corporation; hereafter referred to as "beads") in the manner described below. The beads were washed with MES buffer (0.1 M MES-NaOH; pH 7.0), the supernatant was removed by centrifugation. This washing process was repeated twice and the beads were then suspended in 75 µl of MES buffer. 100 µl of CTL epitope peptide solution (1 mg/ml), and 5 µl of 10 mg/ml EDC (1-ethyl-3-(3-dimethylaminopropyl)carbodiimide hydrochloride) solution was added into beads suspension then mixed well. Thereafter, the reaction was performed at 30° C. in the dark overnight. After the removal of supernatant by centrifugation on the following day, 125 µl of 1 M Tris-HCl was added, and incubation was carried out at 30° C. in the dark for 30 minutes. After the supernatant was removed again, the beads were washed twice with wash buffer (PBS(-), 0.05% Tween 20) and were suspended in Immunoblock (DS Pharma Biomedical Co., Ltd.). Thus, immobilization of the CTL epitope peptide was completed.

Example 4

Measurement of CTL-epitope Specific IgG Antibody Titer

The peptides having 5 linked epitopes according to the present invention were dissolved in Otsuka distilled water (Otsuka Pharmaceutical Factory Inc.) at 2 mg/ml, and the resulting solution was filled into a B Braun Injekt syringe. After the equivalent amount of IFA was filled into another syringe, these syringes were connected to each other using a GP syringe connector, and a solution of the peptides having 5 linked epitopes was thoroughly mixed with IFA to prepare an emulsion. The emulsion was weekly administered in amounts of 100 µl each in the vicinity of base of tale of CBF1 mice (C57BL/6×Balb/c F1), and administration was carried out three times in total. The blood was collected from mice 1 week after the final administration to obtain serum samples. As control samples, emulsions were prepared using peptide mixtures of PEP2, PEP3, PEP4, PEP5, and PEP7 (1 mg/ml each), and the resulting emulsions were administered in accordance with the same schedule as with the peptide having 5 linked epitopes (the mixture-administered group).

The CTL epitope peptide-immobilized beads diluted with Immunoblock were dispensed into wells of a 96-well filter plate. The dispensed beads were washed with a wash buffer, subsequently 100 µl of mouse serum samples diluted 200-fold with Immunoblock were added into each wells. The plate was incubated for 90 minutes at 30° C. with 600 rpm mixing. After the three times of plate washing with a wash buffer, 100 µl of biotinylated-anti-mouse IgG (H+L) (Vector Laboratories) diluted 500-fold with Immunoblock was added into each well, and the plate was incubated for 60 minutes at 30° C. with 600 rpm mixing After the three times of plate washing with a wash buffer, 100 µl of streptavidin-R-phycoerythrin conjugate (Invitrogen) diluted 500-fold with Immunoblock was added into each well, and the plate was incubated for 30 minutes at 30° C. with 600 rpm mixing. After the three times of plate washing with a wash buffer, 100 µl of wash buffer was added into each well to suspend beads, and the mean fluorescence intensity of PE which specifically bound to relevant beads was measured using the Bio-Plex Suspension Array System (BIO-RAD).

The results of measurement of the CTL-epitope specific IgG titer are as shown in FIG. 2. FIG. 2 shows the degree of the CTL epitope peptide specific IgG antibody production compared with that of negative control group (hereafter abbreviated as the "IFA group") mice. The results from IFA group mice which were administrated emulsion prepared by mixing equivalent amounts of IFA and Otsuka distilled water (Otsuka Pharmaceutical Factory Inc.) were compared with the results which were obtained in accordance with the same treatment schedule as that of the CTL epitope peptide mixture or the peptide having 5 linked epitopes.

As shown in FIG. 2, the induction of the CTL epitope specific IgG antibody production was not observed in the mixture-administered group, compared with the IFA group. In contrast, strong induction of CTL epitope specific IgG antibody production was observed frequently when the peptide having 5 linked epitopes was administered. In addition, the amount of IgG production was found to be significantly higher (e.g., several ten times to several hundred times higher) depending on the type of the peptide having 5 linked epitopes administered. In the case of a peptide comprising 5 epitopes linked to each other in the order such as TPV17, multiple CTL epitope specific IgG antibodies production was not induced.

These results demonstrate that administration of the peptide having 5 linked epitopes can more strongly activate antitumor immunity than administration of a mixture of CTL epitope peptides constituting the peptide having 5 linked epitopes.

For a cancer patient who has been treated with a peptide vaccine for cancer, induction of CTL epitope peptide specific IgG production and induction of epitope peptide specific CTL are both effective for life prolongation. Accordingly, the life prolongation effects attained by the present invention are superior to those attained by cancer treatment using peptide vaccines comprising known CTL epitope peptides or mixtures thereof. Therefore, the peptide having 5 linked epitopes according to the present invention can be suitably used as a therapeutic and/or preventive agent for cancers or diseases caused thereby and peptide vaccines for cancer that can provide superior treatment outcomes compared with cancer treatment using peptide vaccines comprising known CTL epitope peptides or mixtures thereof.

All publications, patents, and patent applications cited herein are incorporated herein by reference in their entirety.

The invention claimed is:

1. A peptide having 5 linked epitopes, wherein the 5 epitopes are selected, optionally redundantly, from the group consisting of CTL epitope peptides: the peptide as shown in SEQ ID NO: 1 (PEP1); the peptide as shown in SEQ ID NO: 2 (PEP2); the peptide as shown in SEQ ID NO: 3 (PEP3); the peptide as shown in SEQ ID NO: 4 (PEP4); the peptide as shown in SEQ ID NO: 5 (PEP5); the peptide as shown in SEQ ID NO: 6 (PEP6); and the peptide as shown in SEQ ID NO: 7 (PEP7); linked via linkers, and the peptide having 5 linked epitopes has one or more features selected from the features (1) to (12) below:
(1) the peptide comprises a sequence composed of PEP5 and PEP2 successively disposed in such order from the N terminus via a linker;
(2) the peptide comprises a sequence composed of PEP2 and PEP4 successively disposed in such order from the N terminus via a linker;
(3) the peptide comprises a sequence composed of PEP4 and PEP6 successively disposed in such order from the N terminus via a linker;
(4) the peptide comprises a sequence composed of PEP6 and PEP3 successively disposed in such order from the N terminus via a linker;
(5) the peptide comprises a sequence composed of PEP4 and PEP1 successively disposed in such order from the N terminus via a linker;
(6) the peptide comprises a sequence composed of PEP1 and PEP3 successively disposed in such order from the N terminus via a linker;
(7) the peptide comprises a sequence composed of PEP4 and PEP2 successively disposed in such order from the N terminus via a linker;
(8) the peptide comprises a sequence composed of PEP1 and PEP4 successively disposed in such order from the N terminus via a linker;
(9) the peptide comprises a sequence composed of PEP5 and PEP1 successively disposed in such order from the N terminus via a linker;
(10) the peptide comprises a sequence composed of PEP6 and PEP5 successively disposed in such order from the N terminus via a linker;
(11) the peptide comprises PEP2 at the C terminus; and
(12) the peptide comprises PEP3 at the C terminus.

2. The peptide having 5 linked epitopes according to claim 1, which comprises a sequence at the N terminus composed of PEP5 and PEP2, PEP6 and PEP5, or PEP4 and PEP6 successively disposed in such order from the N terminus via a linker and/or a sequence at the C terminus composed of PEP7 and PEP3, PEP4 and PEP3, PEP6 and PEP3, PEP1 and PEP3, PEP5 and PEP2, PEP4 and PEP2, or PEP5 and PEP3 successively disposed in such order from the N terminus via a linker.

3. The peptide having 5 linked epitopes according to claim 2, which comprises a sequence selected from the sequences (a) to (p) below:
(a) PEP5-PEP2-PEP4-PEP7-PEP3;
(b) PEP5-PEP2-PEP7-PEP3-PEP4;
(c) PEP4-PEP6-PEP5-PEP7-PEP3;
(d) PEP5-PEP2-PEP4-PEP6-PEP3;
(e) PEP5-PEP2-PEP4-PEP1-PEP3;
(f) PEP4-PEP5-PEP2-PEP7-PEP3;
(g) PEP7-PEP3-PEP4-PEP5-PEP2;
(h) PEP5-PEP7-PEP3-PEP4-PEP2;
(i) PEP6-PEP1-PEP4-PEP5-PEP2;
(j) PEP6-PEP5-PEP1-PEP4-PEP2;
(k) PEP4-PEP5-PEP1-PEP6-PEP3;
(l) PEP7-PEP2-PEP4-PEP5-PEP3;
(m) PEP4-PEP2-PEP7-PEP5-PEP3;
(n) PEP7-PEP2-PEP5-PEP4-PEP3;
(o) PEP5-PEP2-PEP7-PEP4-PEP3; or
(p) PEP5-PEP2-PEP4-PEP3-PEP7,
wherein "-" represents a linker.

4. The peptide having 5 linked epitopes according to claim 1, wherein the linker is an amino acid linker.

5. The peptide having 5 linked epitopes according to claim 4, wherein the amino acid linker is an arginine dimer composed of two arginine residues linked to each other.

6. A combination of CTLs obtained by stimulating peripheral blood lymphocytes using the peptide having 5 linked epitopes according to claim 1.

* * * * *

SEQUENCE LISTING

```
<160> NUMBER OF SEQ ID NOS: 27

<210> SEQ ID NO 1
<211> LENGTH: 9
<212> TYPE: PRT
<213> ORGANISM: Homo sapiens

<400> SEQUENCE: 1

Lys Leu Val Glu Arg Leu Gly Ala Ala
1               5

<210> SEQ ID NO 2
<211> LENGTH: 9
```

```
<212> TYPE: PRT
<213> ORGANISM: Homo sapiens

<400> SEQUENCE: 2

Ala Ser Leu Asp Ser Asp Pro Trp Val
1               5

<210> SEQ ID NO 3
<211> LENGTH: 9
<212> TYPE: PRT
<213> ORGANISM: Homo sapiens

<400> SEQUENCE: 3

Leu Leu Gln Ala Glu Ala Pro Arg Leu
1               5

<210> SEQ ID NO 4
<211> LENGTH: 9
<212> TYPE: PRT
<213> ORGANISM: Homo sapiens

<400> SEQUENCE: 4

Asp Tyr Ser Ala Arg Trp Asn Glu Ile
1               5

<210> SEQ ID NO 5
<211> LENGTH: 10
<212> TYPE: PRT
<213> ORGANISM: Homo sapiens

<400> SEQUENCE: 5

Val Tyr Asp Tyr Asn Cys His Val Asp Leu
1               5                   10

<210> SEQ ID NO 6
<211> LENGTH: 9
<212> TYPE: PRT
<213> ORGANISM: Homo sapiens

<400> SEQUENCE: 6

Leu Tyr Ala Trp Glu Pro Ser Phe Leu
1               5

<210> SEQ ID NO 7
<211> LENGTH: 9
<212> TYPE: PRT
<213> ORGANISM: Homo sapiens

<400> SEQUENCE: 7

Gln Ile Arg Pro Ile Phe Ser Asn Arg
1               5

<210> SEQ ID NO 8
<211> LENGTH: 9
<212> TYPE: PRT
<213> ORGANISM: Homo sapiens

<400> SEQUENCE: 8

Arg Met Phe Pro Asn Ala Pro Tyr Leu
1               5

<210> SEQ ID NO 9
<211> LENGTH: 9
<212> TYPE: PRT
<213> ORGANISM: Homo sapiens
```

-continued

<400> SEQUENCE: 9

Thr Tyr Leu Pro Thr Asn Ala Ser Leu
1               5

<210> SEQ ID NO 10
<211> LENGTH: 54
<212> TYPE: PRT
<213> ORGANISM: Artificial
<220> FEATURE:
<223> OTHER INFORMATION: synthetic peptide

<400> SEQUENCE: 10

Val Tyr Asp Tyr Asn Cys His Val Asp Leu Arg Arg Ala Ser Leu Asp
1               5                   10                  15

Ser Asp Pro Trp Val Arg Arg Asp Tyr Ser Ala Arg Trp Asn Glu Ile
            20                  25                  30

Arg Arg Gln Ile Arg Pro Ile Phe Ser Asn Arg Arg Leu Leu Gln
        35                  40                  45

Ala Glu Ala Pro Arg Leu
    50

<210> SEQ ID NO 11
<211> LENGTH: 54
<212> TYPE: PRT
<213> ORGANISM: Artificial
<220> FEATURE:
<223> OTHER INFORMATION: synthetic peptide

<400> SEQUENCE: 11

Val Tyr Asp Tyr Asn Cys His Val Asp Leu Arg Arg Ala Ser Leu Asp
1               5                   10                  15

Ser Asp Pro Trp Val Arg Arg Gln Ile Arg Pro Ile Phe Ser Asn Arg
            20                  25                  30

Arg Arg Leu Leu Gln Ala Glu Ala Pro Arg Leu Arg Arg Asp Tyr Ser
        35                  40                  45

Ala Arg Trp Asn Glu Ile
    50

<210> SEQ ID NO 12
<211> LENGTH: 54
<212> TYPE: PRT
<213> ORGANISM: Artificial
<220> FEATURE:
<223> OTHER INFORMATION: synthetic peptide

<400> SEQUENCE: 12

Asp Tyr Ser Ala Arg Trp Asn Glu Ile Arg Arg Leu Tyr Ala Trp Glu
1               5                   10                  15

Pro Ser Phe Leu Arg Arg Val Tyr Asp Tyr Asn Cys His Val Asp Leu
            20                  25                  30

Arg Arg Gln Ile Arg Pro Ile Phe Ser Asn Arg Arg Leu Leu Gln
        35                  40                  45

Ala Glu Ala Pro Arg Leu
    50

<210> SEQ ID NO 13
<211> LENGTH: 54
<212> TYPE: PRT
<213> ORGANISM: Artificial
<220> FEATURE:
<223> OTHER INFORMATION: synthetic peptide

<400> SEQUENCE: 13

Val Tyr Asp Tyr Asn Cys His Val Asp Leu Arg Arg Ala Ser Leu Asp
1               5                   10                  15

Ser Asp Pro Trp Val Arg Arg Asp Tyr Ser Ala Arg Trp Asn Glu Ile
            20                  25                  30

Arg Arg Leu Tyr Ala Trp Glu Pro Ser Phe Leu Arg Arg Leu Leu Gln
        35                  40                  45

Ala Glu Ala Pro Arg Leu
    50

<210> SEQ ID NO 14
<211> LENGTH: 54
<212> TYPE: PRT
<213> ORGANISM: Artificial
<220> FEATURE:
<223> OTHER INFORMATION: synthetic peptide

<400> SEQUENCE: 14

Val Tyr Asp Tyr Asn Cys His Val Asp Leu Arg Arg Ala Ser Leu Asp
1               5                   10                  15

Ser Asp Pro Trp Val Arg Arg Asp Tyr Ser Ala Arg Trp Asn Glu Ile
            20                  25                  30

Arg Arg Lys Leu Val Glu Arg Leu Gly Ala Ala Arg Arg Leu Leu Gln
        35                  40                  45

Ala Glu Ala Pro Arg Leu
    50

<210> SEQ ID NO 15
<211> LENGTH: 54
<212> TYPE: PRT
<213> ORGANISM: Artificial
<220> FEATURE:
<223> OTHER INFORMATION: synthetic peptide

<400> SEQUENCE: 15

Asp Tyr Ser Ala Arg Trp Asn Glu Ile Arg Arg Val Tyr Asp Tyr Asn
1               5                   10                  15

Cys His Val Asp Leu Arg Arg Ala Ser Leu Asp Ser Asp Pro Trp Val
            20                  25                  30

Arg Arg Gln Ile Arg Pro Ile Phe Ser Asn Arg Arg Leu Leu Gln
        35                  40                  45

Ala Glu Ala Pro Arg Leu
    50

<210> SEQ ID NO 16
<211> LENGTH: 54
<212> TYPE: PRT
<213> ORGANISM: Artificial
<220> FEATURE:
<223> OTHER INFORMATION: synthetic peptide

<400> SEQUENCE: 16

Gln Ile Arg Pro Ile Phe Ser Asn Arg Arg Leu Leu Gln Ala Glu
1               5                   10                  15

Ala Pro Arg Leu Arg Arg Asp Tyr Ser Ala Arg Trp Asn Glu Ile Arg
            20                  25                  30

Arg Val Tyr Asp Tyr Asn Cys His Val Asp Leu Arg Arg Ala Ser Leu
        35                  40                  45

Asp Ser Asp Pro Trp Val

<210> SEQ ID NO 17
<211> LENGTH: 54
<212> TYPE: PRT
<213> ORGANISM: Artificial
<220> FEATURE:
<223> OTHER INFORMATION: synthetic peptide

<400> SEQUENCE: 17

Val Tyr Asp Tyr Asn Cys His Val Asp Leu Arg Arg Gln Ile Arg Pro
1               5                   10                  15

Ile Phe Ser Asn Arg Arg Arg Leu Leu Gln Ala Glu Ala Pro Arg Leu
            20                  25                  30

Arg Arg Asp Tyr Ser Ala Arg Trp Asn Glu Ile Arg Arg Ala Ser Leu
        35                  40                  45

Asp Ser Asp Pro Trp Val
    50

<210> SEQ ID NO 18
<211> LENGTH: 54
<212> TYPE: PRT
<213> ORGANISM: Artificial
<220> FEATURE:
<223> OTHER INFORMATION: synthetic peptide

<400> SEQUENCE: 18

Leu Tyr Ala Trp Glu Pro Ser Phe Leu Arg Arg Lys Leu Val Glu Arg
1               5                   10                  15

Leu Gly Ala Ala Arg Arg Asp Tyr Ser Ala Arg Trp Asn Glu Ile Arg
            20                  25                  30

Arg Val Tyr Asp Tyr Asn Cys His Val Asp Leu Arg Arg Ala Ser Leu
        35                  40                  45

Asp Ser Asp Pro Trp Val
    50

<210> SEQ ID NO 19
<211> LENGTH: 54
<212> TYPE: PRT
<213> ORGANISM: Artificial
<220> FEATURE:
<223> OTHER INFORMATION: synthetic peptide

<400> SEQUENCE: 19

Leu Tyr Ala Trp Glu Pro Ser Phe Leu Arg Arg Val Tyr Asp Tyr Asn
1               5                   10                  15

Cys His Val Asp Leu Arg Arg Lys Leu Val Glu Arg Leu Gly Ala Ala
            20                  25                  30

Arg Arg Asp Tyr Ser Ala Arg Trp Asn Glu Ile Arg Arg Ala Ser Leu
        35                  40                  45

Asp Ser Asp Pro Trp Val
    50

<210> SEQ ID NO 20
<211> LENGTH: 54
<212> TYPE: PRT
<213> ORGANISM: Artificial
<220> FEATURE:
<223> OTHER INFORMATION: synthetic peptide

<400> SEQUENCE: 20

Asp Tyr Ser Ala Arg Trp Asn Glu Ile Arg Arg Val Tyr Asp Tyr Asn

```
                1               5                   10                  15
Cys His Val Asp Leu Arg Arg Lys Leu Val Glu Arg Leu Gly Ala Ala
                20                  25                  30

Arg Arg Leu Tyr Ala Trp Glu Pro Ser Phe Leu Arg Arg Leu Leu Gln
        35                  40                  45

Ala Glu Ala Pro Arg Leu
    50

<210> SEQ ID NO 21
<211> LENGTH: 54
<212> TYPE: PRT
<213> ORGANISM: Artificial
<220> FEATURE:
<223> OTHER INFORMATION: synthetic peptide

<400> SEQUENCE: 21

Gln Ile Arg Pro Ile Phe Ser Asn Arg Arg Ala Ser Leu Asp Ser
1               5                   10                  15

Asp Pro Trp Val Arg Arg Asp Tyr Ser Ala Arg Trp Asn Glu Ile Arg
                20                  25                  30

Arg Val Tyr Asp Tyr Asn Cys His Val Asp Leu Arg Arg Leu Leu Gln
        35                  40                  45

Ala Glu Ala Pro Arg Leu
    50

<210> SEQ ID NO 22
<211> LENGTH: 54
<212> TYPE: PRT
<213> ORGANISM: Artificial
<220> FEATURE:
<223> OTHER INFORMATION: synthetic peptide

<400> SEQUENCE: 22

Asp Tyr Ser Ala Arg Trp Asn Glu Ile Arg Arg Ala Ser Leu Asp Ser
1               5                   10                  15

Asp Pro Trp Val Arg Arg Gln Ile Arg Pro Ile Phe Ser Asn Arg Arg
                20                  25                  30

Arg Val Tyr Asp Tyr Asn Cys His Val Asp Leu Arg Arg Leu Leu Gln
        35                  40                  45

Ala Glu Ala Pro Arg Leu
    50

<210> SEQ ID NO 23
<211> LENGTH: 54
<212> TYPE: PRT
<213> ORGANISM: Artificial
<220> FEATURE:
<223> OTHER INFORMATION: synthetic peptide

<400> SEQUENCE: 23

Gln Ile Arg Pro Ile Phe Ser Asn Arg Arg Ala Ser Leu Asp Ser
1               5                   10                  15

Asp Pro Trp Val Arg Arg Val Tyr Asp Tyr Asn Cys His Val Asp Leu
                20                  25                  30

Arg Arg Asp Tyr Ser Ala Arg Trp Asn Glu Ile Arg Arg Leu Leu Gln
        35                  40                  45

Ala Glu Ala Pro Arg Leu
    50

<210> SEQ ID NO 24
```

<211> LENGTH: 54
<212> TYPE: PRT
<213> ORGANISM: Artificial
<220> FEATURE:
<223> OTHER INFORMATION: synthetic peptide

<400> SEQUENCE: 24

Val Tyr Asp Tyr Asn Cys His Val Asp Leu Arg Arg Ala Ser Leu Asp
1               5                   10                  15

Ser Asp Pro Trp Val Arg Arg Gln Ile Arg Pro Ile Phe Ser Asn Arg
            20                  25                  30

Arg Arg Asp Tyr Ser Ala Arg Trp Asn Glu Ile Arg Arg Leu Leu Gln
        35                  40                  45

Ala Glu Ala Pro Arg Leu
    50

<210> SEQ ID NO 25
<211> LENGTH: 54
<212> TYPE: PRT
<213> ORGANISM: Artificial
<220> FEATURE:
<223> OTHER INFORMATION: synthetic peptide

<400> SEQUENCE: 25

Val Tyr Asp Tyr Asn Cys His Val Asp Leu Arg Arg Ala Ser Leu Asp
1               5                   10                  15

Ser Asp Pro Trp Val Arg Arg Asp Tyr Ser Ala Arg Trp Asn Glu Ile
            20                  25                  30

Arg Arg Leu Leu Gln Ala Glu Ala Pro Arg Leu Arg Arg Gln Ile Arg
        35                  40                  45

Pro Ile Phe Ser Asn Arg
    50

<210> SEQ ID NO 26
<211> LENGTH: 54
<212> TYPE: PRT
<213> ORGANISM: Artificial
<220> FEATURE:
<223> OTHER INFORMATION: synthetic peptide

<400> SEQUENCE: 26

Ala Ser Leu Asp Ser Asp Pro Trp Val Arg Arg Leu Leu Gln Ala Glu
1               5                   10                  15

Ala Pro Arg Leu Arg Arg Asp Tyr Ser Ala Arg Trp Asn Glu Ile Arg
            20                  25                  30

Arg Val Tyr Asp Tyr Asn Cys His Val Asp Leu Arg Arg Gln Ile Arg
        35                  40                  45

Pro Ile Phe Ser Asn Arg
    50

<210> SEQ ID NO 27
<211> LENGTH: 54
<212> TYPE: PRT
<213> ORGANISM: Artificial
<220> FEATURE:
<223> OTHER INFORMATION: synthetic peptide

<400> SEQUENCE: 27

Gln Ile Arg Pro Ile Phe Ser Asn Arg Arg Ala Ser Leu Asp Ser
1               5                   10                  15

Asp Pro Trp Val Arg Arg Val Tyr Asp Tyr Asn Cys His Val Asp Leu
            20                  25                  30

```
Arg Arg Leu Leu Gln Ala Glu Ala Pro Arg Leu Arg Arg Asp Tyr Ser
        35                  40                  45
Ala Arg Trp Asn Glu Ile
    50
```